United States Patent [19]

Cooley

[11] 3,937,806

[45] Feb. 10, 1976

[54] ORAL COMPOSITIONS FOR CARIES PROPHYLAXIS

[75] Inventor: William Edward Cooley, Wyoming, Ohio

[73] Assignee: The Procter & Gamble Company, Cincinnati, Ohio

[22] Filed: May 7, 1974

[21] Appl. No.: 467,693

Related U.S. Application Data

[63] Continuation-in-part of Ser. No. 52,774, July 6, 1970, which is a continuation-in-part of Ser. No. 848,081, Aug. 6, 1969, abandoned, which is a continuation-in-part of Ser. No. 737,328, June 17, 1968, abandoned, which is a continuation-in-part of Ser. No. 546,511, May 2, 1966, abandoned.

[52] U.S. Cl. ................................................ 424/52
[51] Int. Cl.$^2$ ......................................... A61K 7/18
[58] Field of Search .............................. 424/49–58

[56] References Cited
UNITED STATES PATENTS 3,070,510  12/1962  Cooley et al. ........................ 424/52

3,175,951  3/1965  Tucker et al. ........................ 424/52

FOREIGN PATENTS OR APPLICATIONS 654,472  6/1951  United Kingdom .................. 424/52

OTHER PUBLICATIONS

Cozzi et al., Z. Electrochem., Vol. 58, pp. 907–912, 1954.

Primary Examiner—Richard L. Huff
Attorney, Agent, or Firm—J. D. Schaeffer; Ronald L. Hemingway; Richard C. Witte

[57] ABSTRACT

Anticariogenic oral compositions such as dentifrices and mouthwashes comprising a water-soluble fluoride salt and an indium (III)-malic acid water-soluble complex as a stable and dental enamel reactive source of indium.

4 Claims, No Drawings

ORAL COMPOSITIONS FOR CARIES PROPHYLAXIS

CROSS-REFERENCE TO RELATED APPLICATIONS

This application is a continuation-in-part of the copending application of William E. Cooley, Ser. No. 52,774, filed July 6, 1970, which in turn is a continuation-in-part of the application of William E. Cooley, Ser. No. 848,081, filed Aug. 6, 1969 (now abandoned), which in turn is a continuation-in-part of the application of William E. Cooley, Ser. No. 737,328, filed June 17, 1968 (now abandoned), which in turn is a continuation-in-part of the application of William E. Cooley, Ser. No. 546,511, filed May 2, 1966 (now abandoned).

BACKGROUND OF THE INVENTION

This invention relates to improved oral compositions useful in caries prophylaxis containing a water-soluble complex of indium (III) and malic acid.

By the term "oral composition" as used herein is meant a product which in the ordinary course of usage is not intentionally ingested, but is retained in the oral cavity for a time sufficient to contact substantially all of the dental surfaces. Such products include, for example, dentifrices, mouthwashes, chewing gums, and dental prophylaxis pastes and topical solutions for application in the dental office. The oral compositions for caries prophylaxis herein contemplated do not require ingestion for anticaries effect.

The efficacy of fluoride in caries prophylaxis is well established, to the extent that the topical application of aqueous solutions of various water-soluble fluorides has become a routine procedure in many dental offices and clinics. Moreover, toothpaste compositions containing certain fluorides have recently been recognized as effective against caries by the American Dental Association.

It is known that certain metallic ions can have a significant effect on the anticariogenic efficacy of fluorides. For example, a body of scientific literature shows that the use of a source of stannous ions in conjunctions with fluoride gives a more effective anticariogenic product than is attained with fluoride alone [J. C. Muhler et al., J.A.D.A. 51, 665 (1955)]. More recently, relatively low concentrations of In(III) have been found to coact with fluorides to provide a high level of anticariogenic activity (U.S. Pat. 3,175,951, granted Mar. 30, 1965).

One of the problems which has developed in the formulation of stable oral compositions containing In(III) is the propensity of this metal to hydrolyze to form insoluble "indium hydroxide" and/or react with other constituents of the composition to form very stable complexes or highly insoluble compounds. The occurrence of any of the foregoing can render the In(III) non-reactive with dental enamel.

Similar problems have been faced in the formulation of oral products containing stannous tin, and various solutions have been posed. For example, Holliday et al., U.S. Pat. No. 3,105,798, granted Oct. 1, 1963, teach the use of aldonate complexes of stannous tin, such as stannous gluconate, to provide a water-soluble source of stannous tin in a stable and enamel-reactive form. Although such complexing anions are useful in conjunction with stannous tin, they do not provide an effective means for preventing hydrolysis of In(III).

SUMMARY OF THE INVENTION

It has now been discovered that In(III) forms a water-soluble complex with the malate ligand which is sufficiently stable to prevent hydrolysis and conversion of In(III) to inactive species, but which is highly reactive with dental enamel.

It is an object of this invention to provide an oral composition which contains effective levels of In(III) in a form which resists hydrolysis and conversion to non-reactive species and is reactive with dental enamel throughout the life of the composition.

These and other objects will become apparent from the following description.

DETAILED DESCRIPTION OF THE INVENTION

In general, this invention comprises aqueous oral compositions for caries prophylaxis containing a water-soluble fluoride salt and an indium-malic acid water-soluble complex as a stable and dental-enamel reactive source of In(III), the pH of said composition being from about 2.5 to 7.0.

A wide variety of fluorides can be used in the compositions of this invention. Specifically, any water-soluble fluoride which is capable of providing at least 25 p.p.m. of fluoride ion in aqueous solution can be used to realize the benefits of this invention.

Among the fluoride salts contemplated for use in this invention are the following:

INORGANIC FLUORIDES

Sodium fluoride
Potassium fluoride
Lithium fluoride
Cesium fluoride
Ammonium fluoride
Aluminum fluoride
Cupric fluoride
Indium fluoride
Lead fluoride
Ferric fluoride
Nickel fluoride
Palladium fluoride
Silver fluoride
Zinc fluoride
Zirconium fluoride

ORGANIC FLUORIDES

I. Water-soluble amine hydrofluorides such as the following:
Hexylamine hydrofluoride
Laurylamine hydrofluoride
Myristylamine hydrofluoride
Decanolamine hydrofluoride
Octadecenylamine hydrofluoride
Myristoxyamine hydrofluoride
Diethylaminoethyloctoylamide hydrofluoride
Diethanolaminoethyloleylamide hydrofluoride
Diethanolaminopropyl-N'-octadecenylamide dihydrofluoride
1-ethanol-2-hexadecylimidazoline dihydrofluoride
Octoylethanolamine hydrofluoride Those compounds of this class which contain at least one hydrocarbon radical such as an alkyl, alkylol, alkenyl or alkylene radical having from 8 to 20 carbon atoms are especially preferred for use in the compositions of this invention because of their surface-active properties. These and other operable amine hydrofluorides as well as a method for their preparation are disclosed by Schmid et al., in U.S. Pat. 3,083,143, granted Mar. 26, 1963.

II. Compounds of the formula $$(HOC_xH_{2x})_n N^+ (C_yH_{2y+1})_{4-n} F^=$$

wherein $x$ and $y$ are each integers from 1 to 4, and $n$ is an integer from 1 to 3. Such compounds include, for example, dimethyldiethanol ammonium fluoride, trimethylethanol ammonium fluoride, and methyltriethanol ammonium fluoride. Further examples and methods of preparing these compounds are found in U.S. Pat. 3,235,459, granted Feb. 15, 1966.

III. Water-soluble additional compounds of amino acids and hydrofluoric acid or fluorides:

Examples of this class of fluorides include:
Betaine hydrofluoride
Sarcosine stannous fluoride
Alanine stannous fluoride
Glycine potassium fluoride
Sarcosine potassium fluoride
Glycine hydrofluoride
Lysine hydrofluoride
Alanine hydrofluoride
Betaine zirconium fluoride Additional operable examples of this class of compounds as well as a method for their preparation are disclosed by Schmid in Canadian Patent 594,553, granted Mar. 15, 1960.

The quantity of fluoride salt employed in the compositions of this invention must be sufficient to provide at least about 25 parts of fluoride ions per million parts of the total composition. Extremely large amounts of fluoride ions do not appreciably enhance the desirable properties of the composition and may cause it to have toxic effects. Accordingly, the compositions of this invention do not contain a total or more than 4,000 parts fluoride ion per million parts of the total composition, and in the case of dentifrice compositions, preferably not more than about 3,000 parts per million.

As hereinbefore stated, the indium-malic acid water soluble complex is an essential component of the compositions of the present invention; however, additional indium can be provided by any water-soluble non-toxic In(III) compound. Preferred supplemental In(III) compounds for the purpose of this invention are $InCl_3$, $In(ClO_4)_3$, $In(NO_3)_3$, $In_2(SO_4)_3$. Mixtures of the foregoing indium compounds can be used to provide indium in the practice of this invention.

Preferably, indium fluoride will be used as a source of at least a portion of the total In(III). In any event, the total In(III) content must be from about 10 to about 7,500 p.p.m., the preferred range being from about 25 to about 4,000 p.p.m., and the most preferred range being from about 100 to about 4,000 p.p.m. If the concentration of In(III) is greater than about 7,500 p.p.m., the reaction of fluoride with the dental enamel will be impaired.

The indium-malic acid water soluble complex is formed by reacting a water-soluble indium salt with malic acid or with a malic acid salt of a cation having a stability constant which is less than the formation constant of the corresponding soluble complex, the molar ratio of malic acid or malic acid salt to indium salt being in a range of from about 1:1 to about 6:1. A molar ratio of 2.98:1 is most preferred. Among the salts of malic acid which can be used to prepare said complex are the alkali metal (e.g., sodium and potassium), ammonium, and substituted ammonium (e.g., mono-, di- and triethanolammonium) salts of malic acid.

The pH of the compositions of this invention lies between about 2.5 and 7, the preferred range being from about 4.0 to 6.5. Above about pH 7 loss of In(III) available for reaction with enamel can be too rapid; and, certain flavoring substances, especially esters, deteriorate rapidly. Too low a pH, below about 2.5, produces an astringent taste which is highly objectionable to most people. It also accelerates the hydrolysis of certain of the sudsing agents thereby producing an unpleasant "fatty acid taste" and reducing the amount of sudsing obtained in use. Furthermore, pH values below 2.5 tend to cause corrosion of metal tubes in which the composition may be stored, and tend to hydrolyze other ingredients such as condensed phosphates if used as abrasives. Such hydrolysis can decrease the availability of In(III) by providing anions with which it can form very stable complexes or with which it can precipitate as highly insoluble compounds.

In addition to water, and the essential ingredients described herein, the compositions of this invention can contain the usual dentifrice, mouthwash, etc., components. For example, toothpastes typically contain an abrasive material, sudsing agent, binders, humectants, flavoring and sweetening materials.

The abrasives preferably should be relatively insoluble and relatively stable at the pH ranges herein specified. They desirably should not be too abrasive so as to scratch the surface of the teeth or unduly abrade the dentin, but they desirably should have just sufficient abrading power to clean the teeth. In the practice of this invention, any dental abrasives can be used which have these properties, and are sufficiently compatible with In(III) ion and fluoride ions.

Preferred abrasives for use in the fluoride-containing dentifrices of this invention include the insoluble condensed phosphates and the water-impervious, cross-linked, thermosetting resins. Examples of such insoluble condensed phosphates include calcium pyrophosphate, insoluble highly polymerized calcium polyphosphate — sometimes called calcium polymetaphosphate, and insoluble highly polymerized sodium polyphosphate — sometimes called insoluble sodium metaphosphate. Examples of operable resin abrasives are the particulate condensation products of formaldehyde with melamine and/or urea, and others fully described in U.S. Pat. 3,070,510, granted Dec. 25, 1962. Mixtures of abrasives can be used.

The total amount of abrasive materials in dentifrices of this invention can range from 0.5% to 95% by weight of the dentifrice. Preferably, toothpastes contain from 20% to 60% by weight, and tooth powders contain from 60% to 95% by weight.

Dentifrices conventionally contain sudsing agents, although these are not critical in the practice of the present invention. Any of the commonly used sudsing agents can be used if they are reasonably stable and form suds within the pH range of the compositions of this invention. Examples of suitable sudsing agents include, but are not limited to, water-soluble alkyl sulfates having alkyl groups of from about 8 to 18 carbon atoms, such as sodium lauryl sulfate; water-soluble salts of sulfonated monoglycerides of fatty acids having from 10 to 18 carbon atoms, such as sodium coconut monoglyceride sulfonate; salts of fatty acid amides of taurines, such as sodium-N-methyl-N-palmitoyl tauride;

salts of fatty acid esters of isethionic acid and substantially saturated aliphatic acyl amides of saturated aliphatic monoaminocarboxylic acids having 2 to 6 carbon atoms and in which the acyl radical contains 12 to 16 carbon atoms, such as sodium N-lauroyl sarcoside. Mixtures of two or more sudsing agents can also be used.

Sudsing agents can be used in the compositions of this invention in an amount of from 0.5% to 5.0% by weight of the total composition.

In preparing toothpastes, it is necessary to add some thickening material. Preferred thickening agents are hydroxyethylcellulose and water-soluble salts of cellulose ethers such as sodium carboxymethylcellulose and sodium carboxymethylhydroxyethylcellulose. Natural gums such as gum karaya, gum arabic, and gum tragacanth also can be used as thickeners, but may tend to cause undesirable odors or flavors in some formulations. Colloidal magnesium aluminum silicate or finely divided silica can be used as a part of the thickening agent for improvement in texture. Thickening agents in an amount of from 0.5% to 5.0% by weight of toothpaste, can be used to form a satisfactory toothpaste.

Suitable humectants include glycerine, sorbitol, and other polyhydric alcohols. The humectants may comprise up to about 35% of the toothpaste composition.

Oral compositions additionally contain small amounts of flavorings, such as oil of wintergreen, oil of peppermint, oil of spearmint, oil of sassafras, and oil of anise. Small amounts of sweetening agents such as saccharin, dextrose, and levulose are also conventionally added to such compositions.

Toothpastes generally contain from about 5% to about 50% water.

The dental enamel reactivity of the indium contained in an oral composition such as a dentifrice can be determined by measuring the amount of In(III) uptake by an enamel sample after exposure to the dentifrice according to the following procedure:

Tooth chips having a surface area of 25 to 35 mm$^2$ are mounted on plastic rods and coated with a dental plastic so that only the enamel surfaces are exposed. The surfaces are cleaned and polished and etched by immersion in a 2M solution of perchloric acid for one minute. The tooth chips are again cleaned and polished and placed in an agar-lactic acid decalcifying medium (comprised of 6% agar of the "pH 5" type in .04N lactic acid) for 48 hours at 5°C.

After exposure to the decalcifying medium, the tooth chips are cleaned and immersed in a slurry comprised of 1 part of the dentifrice to be tested and 3 parts of saliva, rotating the chips in the slurry at about 200 r.p.m. for 21 minutes. The treated chips are rinsed in distilled water, the dental plastic is removed and the dentin portion of the tooth chips is ground off from the underside of the chips so that only the treated dental enamel remains.

The dental enamel is analyzed for In and this value is expressed in micrograms per square centimeter ($\mu g/cm^2$).

The stability of the dentifrice on storage with respect to supplying available In(III) to react with dental enamel can be measured as a function of the age of the dentifrice in the following manner.

After specified intervals of time, soluble In(III) is determined by mixing 1 part of the dentifrice with 3 parts of distilled water for 10 minutes. The solids are then removed by centrifugation for 30 minutes at 12,000 r.p.m. and the In(III) concentration in an aliquot of the supernatant is determined by emission spectrography. Results are reported as parts soluble In(III) per million.

The following examples illustrate the invention with greater particularity.

EXAMPLE I

The following toothpaste composition is prepared by conventional methods:

| Ingredient | % by Weight |
| --- | --- |
| Calcium pyrophosphate | 40.00 |
| Sorbitol (70% aqueous solution) | 20.00 |
| Glycerine | 10.00 |
| Sodium coconut monoglyceride sulfonate | 0.81 |
| Sodium lauryl sulfate | 0.70 |
| Sodium carboxymethylcellulose | 1.00 |
| Magnesium aluminum silicate | 0.40 |
| Saccharin | 0.12 |
| Flavor | 0.85 |
| Color | 0.48 |
| Indium fluoride (InF$_3$ . 3H$_2$O) | 0.40 |
| Malic acid | 0.727 |
| Water | balance |
| Total In(III) | 2,088 ppm |
| Molar ratio of malic acid anion to total In(III) | 2.98:1 |
| pH 4.8 | |

The indium-malic acid water-soluble complex is formed in situ during the preparation of the formulation by conventional methods. Substantially the same results are obtained by pre-forming the complex prior to incorporation into the above composition.

The composition of this example is found to yield good In(III) uptake values when tested in the manner hereinbefore described. Effective levels of soluble In(III) are detected in the composition after aging for one year.

Regular use of this product in the conventional manner yields substantial reductions in caries incidence.

Additional toothpaste embodiments of this invention are set forth below:

| Ingredient | EXAMPLES II % by Weight | III % by Weight |
| --- | --- | --- |
| Calcium pyrophosphate | 40.00 | 40.00 |
| Sorbitol (70% aqueous solution) | 20.00 | 20.00 |
| Glycerine | 10.00 | 10.00 |
| Sodium coconut mono-glyceride sulfonate | 0.81 | 0.81 |
| Sodium lauryl sulfate | 0.70 | 0.70 |
| Sodium carboxymethylcellulose | 1.10 | 1.10 |
| Magnesium aluminum silicate | 0.40 | 0.40 |
| Saccharin | 0.12 | 0.12 |
| Flavor | 0.85 | 0.85 |
| Color (0.1% aqueous solution) | 0.48 | 0.48 |
| Methyltriethanolammonium fluoride | 0.96 | |
| Sodium fluoride | | 0.22 |
| Indium chloride InCl$_3$ | | 0.25 |
| Indium perchlorate [In(ClO$_4$)$_3$] | 0.45 | |
| Malic acid | 0.15 | 0.91 |
| Water | balance | |
| Total In(III) (ppm) | 1,250 | 1,300 |
| Molar ratio of complexing acid anion to total In(III) | 1:1 | 6:1 |
| pH adjusted to | 4.8 | 5.2 |

The indium-malic acid water-soluble complex is formed in situ. As disclosed in Example I, similar results are obtained by pre-forming the complex.

Each of the above compositions contains effective levels of dental enamel-reactive In(III) for periods up to one year. These compositions provide an effective means for caries prophylaxis when used in the conventional manner.

EXAMPLE IV

A conventional mouthwash in accordance with this invention is prepared having the following composition:

| Ingredient | % by Weight |
|---|---|
| Ethyl alcohol | 16.00 |
| Glycerine | 10.00 |
| Indium fluoride (InF$_3$ . 3$_2$O) | 0.01925 |
| Malic acid | 0.03500 |
| Flavoring | 0.08 |
| Saccharin | 0.04 |
| Water | balance |
| Total In(III) | 100 ppm |
| Molar ratio of malic acid ion to total In(III) | 2.98:1 |
| pH adjusted to 4.5 | |

The indium-malic acid water-soluble complex is formed in situ. A pre-formed complex gives substantially similar results when added to the formulation.

This mouthwash contains stable levels of enamel-reactive In(III) over a long period of time and yields a significant reduction in enamel solubility.

What is claimed is:

1. An oral composition for caries prophylaxis comprising (1) a water-soluble fluoride salt in a quantity sufficient to provide from about 100 to about 4000 p.p.m. of fluoride ion, and (2) an indium-malic acid water-soluble complex, the molar ratio of malic acid to indium being in a range of from about 1:1 to about 6:1, said composition having a total In(III) content of from about 10 to about 7,500 p.p.m. and a pH in the range from about 4.0 to 6.5.

2. The composition of claim 1 wherein the indium-malic acid water-soluble complex has a molar ratio of 2.98:1 of malic acid to indium.

3. The composition of claim 1 wherein the water-soluble fluoride is indium fluoride.

4. The composition of claim 1 wherein the water-soluble fluoride is sodium fluoride.

* * * * *